(12) United States Patent
Lee et al.

(10) Patent No.: US 7,361,683 B2
(45) Date of Patent: Apr. 22, 2008

(54) PACLITAXEL AQUEOUS INJECTION SOLUTION AND METHODS FOR PREPARING THE SAME

(75) Inventors: Fang-Yu Lee, Taichung Hsien (TW); Shan-Chiung Chen, Taichung Hsien (TW); Bin-Ken Chen, Taichung Hsien (TW); Chiung-Ju Tsai, Taichung Hsien (TW); Yuan-Ken Lin, Taichung Hsien (TW)

(73) Assignee: Yung Shin Pharm. Ind., Co., Ltd (TW)

( * ) Notice: Subject to any disclaimer, the term of this patent is extended or adjusted under 35 U.S.C. 154(b) by 531 days.

(21) Appl. No.: 10/995,262

(22) Filed: Nov. 24, 2004

(65) Prior Publication Data

US 2006/0111432 A1    May 25, 2006

(51) Int. Cl.
*A61K 31/335* (2006.01)
(52) U.S. Cl. .................................................. 514/449
(58) Field of Classification Search ..................... None
See application file for complete search history.

(56) References Cited

U.S. PATENT DOCUMENTS

| 5,504,102 A | 4/1996 | Agharkar et al. |
| 5,733,888 A | 3/1998 | Carver et al. |
| 5,972,992 A | 10/1999 | Carver et al. |
| 5,977,164 A | 11/1999 | Carver et al. |
| 6,140,359 A | 10/2000 | Carver et al. |

FOREIGN PATENT DOCUMENTS

EP    0 835 657 A1    4/1998

OTHER PUBLICATIONS

Praxair, Inc. Product Brochure, "Carbon Dioxide Water Treatment Systems", 1997.*

* cited by examiner

*Primary Examiner*—Ardin H. Marschel
*Assistant Examiner*—James D. Anderson
(74) *Attorney, Agent, or Firm*—Fei-Fei Chao; Andrews Kurth LLP

(57) ABSTRACT

The present invention provides an injectable pharmaceutical composition containing, as an active ingredient, paclitaxel, an anti-cancer agent. The injectable pharmaceutical composition comprises an effective amount of paclitaxel, which is dissolved in polyoxyethylated castor oil, alcohol, and an injectable aqueous solution. A sufficient amount of $CO_2$ is added to stabilize paclitaxel in the injectable pharmaceutical composition to make the injectable pharmaceutical composition to a pH about 5.0.

15 Claims, 2 Drawing Sheets

PACLITAXEL AQUEOUS INJECTION SOLUTION AND METHODS FOR PREPARING THE SAME

FIELD OF THE INVENTION

The present invention relates to a stable injectable pharmaceutical composition (i.e., paclitaxel aqueous injection solution) containing, as an active ingredient, paclitaxel, an anti-cancer agent. The injectable pharmaceutical composition comprises an effective amount of paclitaxel, which is dissolved in polyoxyethylated castor oil, alcohol, and an injectable aqueous solution, preferably water. A sufficient amount of $CO_2$ is added to the injectable pharmaceutical composition to allow the injectable aqueous solution of the injectable pharmaceutical composition to be adjusted to a pH of $\leq 5.0$. The present invention also relates to methods for preparing and using the injectable pharmaceutical composition. The stable injectable pharmaceutical composition is particularly suitable for use in treating patients with breast cancer, ovarian cancer, lung cancer, melanoma, and lymphoma.

BACKGROUND OF THE INVENTION

Paclitaxel, having a chemical name of 5β-20-Epoxy-1, 2α,4,7β,10β,13α-hexahydroxytax-11-en-9-on,4,10 diacetate 2-benzate 13-ester with (2R,3S)-N-benzoyl-3-phenylisoserine, is a naturally occurring compound which has shown great promise as an anti-cancer drug. It is a unique diterpene compound derived from the bark of the *Taxus brevifolia* (Pacific yew) tree. As early as in 1971, paclitaxel was discovered in the crude extract of the bark of the yew tree through a routine preclinical tumor screening program at the National Cancer Institute of the National Institutes of Health, and found to be an effective antileukemic and antitumor agent. See Wani et al, Plant antitumor agents, VI: The Isolation and Structure of Paclitaxel, a Novel Antileukemic and Antitumor Agent from *Taxus brevifolia*, J. Am. Chem. Soc., 93:2325-2327 (1971).

Paclitaxel inhibits rapidly dividing cancer cells by stabilizing microtubule during the cell division and arresting the mitotic spindles. The cancer cells are arrested in the $G_2$ or M phases until the cancer cell death. While most of the well-known mitotic spindle poisons (such as colchicines and podophyllotoxin) inhibit microtubule assembly, paclitaxel employs a different mechanism of action by shifting the equilibrium of polymerimization/depolymerization toward polymer assembly and stabilizing microtubules against depolymerization under conditions which would cause rapid disaggregation of microbubules. The interference with the polymerization/depolymerization cycle in cells appears to interfere with both the relication and migration of cells. Paclitaxel has demonstrated good response rates in treating both ovarian and breast cancer patients and has shown encouraging results in patients with other types cancer including lung, melanoma, lymphoma, head and neck.

Paclitaxel is poorly soluble in water (less than 0.01 mg/mL) and other common vehicles used for the parenteral administration of drugs. Certain organic solvents, however, may at least partially dissolve paclitaxel. However, when a water-miscible organic solvent containing paclitaxel at near its saturation solubility is diluted with aqueous infusion fluid, the drug may precipitate.

Consequently, the commercial products of paclitaxel incorporate a co-solvent system containing a mixture of a polar solvent and a non-ionic solvent, such as a mixture of a polyethylene glycol and Cremophor® EL. Cremophor® EL is the tradename of a condensation product of castor oil and ethylene oxide sold by BASF (Badische Anilin und Soda Fabrik AG, Ludwigshafen, Federal Republic of Germany). Another suitable co-solvent system for paclitaxel is a 50:50 mixture of ethanol and Cremophor® EL. At the present time, PDR (Physicians Desk Reference) recommends that paclitaxel be dissolved in 52.7% Cremophor® EL 49.7% (v/v) dehydrated alcohol, and further diluted in NS (normal saline) or D5W (5% dextrose in water) to a final concentration of 5% Cremophor® EL and 5% dehydrated alcohol or less, for the intravenous administration of the drug to humans.

Paclitaxel for injection concentrate is currently available from Bristol-Myers Squibb Co. (New York, N.Y.) in 30-mg (5-mL) single-dose vials. Each milliliter of formulation contains approximately 6 mg Paclitaxel, 527 mg of Cremophor® EL, and 49.7% (v/v) dehydrated alcohol. This concentrated formulation must be further diluted with NS, D5W, D5NS (normal saline, 5% dextrose in water and 5% dextrose in normal saline) or D5W-R (Ringer's solution with 5% dextrose in water) prior to administration.

It has been noted that the Cremophor/ethanol formulation of paclitaxel precipitates upon dilution with infusion fluid, and fibrous precipitates formed in some compositions during storage for extended periods of time. (See U.S. Pat. No. 5,504,102). Thus, although the ethanol and Cremophor® EL co-solvent system is effective in solubilizing sufficient amounts of the paclitaxel, the resulting composition has been shown to have a limited shelf life. During storage for extended periods of time, the potency or pharmaceutical activity of the composition can decrease as much as 60%.

It has also been discovered that the commercial grade Cremophor® EL with ethanol as a co-solvent, although effective in solubilizing pharmaceutical agents, produces injection compositions that exhibit instability over extended periods of time. In particular, paclitaxel in 52.7 mg/mL: 49.7% of Cremophor® EL and dehydrated ethanol exhibit a 13.3% loss of potency after storage at 40° C. for 7 days (See U.S. Pat. No. 6,140,359) and a loss of potency of greater than 60% after storage for 12 weeks at 50° C. and a loss of potency to 86.7% at 40° C. for seven days (See U.S. Pat. No. 6,140,359). The loss of potency is attributed to the decomposition of paclitaxel during storage.

It is, therefore, a need for a paclitaxel formulation to overcome the stability problems associated with conventional paclitaxel formulations as noted above and as known to one of skill in the art. Recently, U.S. Pat. No. 5,504,102 discloses a way to reduce the decomposition of paclitaxel in Cremophor® EL by reducing the carboxylate anion content with an aluminum oxide bed or by the addition of an acid and particularly a mineral acid such as HCl or $HNO_3$. It is believed that the carboxylate anions in Cremophor® EL cause the degradation of paclitaxel.

U.S. Pat. Nos. 5,733,888, 5,972,992, 5,977,164, and 6,140,359 similarly disclose that the addition of an acidifying agent to polyoxyethylated castor oil to a pH of less than 8.1 and preferably within a pH range of 5 to 7 can prolong the shelf life of a paclitaxel formulation. The preferred acidifying agent is an anhydrous citric acid.

In the invention to be described in the following sections, a novel injectable pharmaceutical composition (i.e., paclitaxel aqueous injection solution) is described. The injectable pharmaceutical composition differs from other paclitaxel aqueous injection solutions currently commercially available in two major aspects: first, it contains a small amount of water in the formulation, as opposed to no water in the commercially available products; and second, the injectable pharmaceutical composition of the present invention is infused with $CO_2$, which can be converted into carbonate ions in the aqueous solution, which in turn act to reduce the pH of the injectable aqueous solution to about $\leq 5.0$. The novel injectable pharmaceutical composition of the present invention demonstrates improved stability and safety as well as prolonged shelf-life for paclitaxel.

SUMMARY OF THE INVENTION

The present invention provides an injectable pharmaceutical composition which comprises an effective amount of paclitaxel; a polyoxyethylated castor oil; an alcohol; and an injectable aqueous solution. A sufficient amount of $CO_2$ is added to the injectable pharmaceutical composition. The $CO_2$ is dissolved in the injectable aqueous solution of the injectable pharmaceutical composition to form carbonate ions, which in turn lower the pH of the injectable aqueous solution to no higher than about 5.0. The amount of $CO_2$ that is sufficient to lower the pH of the injectable aqueous solution to about $\leq 5.0$, and is at least about 0.4 mg of $CO_2$ per mL of the injectable pharmaceutical composition. The suitable form of $CO_2$ used in the preparation is dry ice or $CO_2$ gas or a mixture of both.

The preferred amount of the injectable aqueous solution used in the injectable pharmaceutical composition is at no less than about 4% by volume, and preferably between 4 to 10% by volume, of the entire injectable pharmaceutical composition. The preferred injectable aqueous solution is water, saline, and 5% dextrose in water. The most favorable injectable aqueous solution is water.

The preferred amount of paclitaxel in the injectable pharmaceutical composition is at about 0.01-1% by weight of the entire injectable pharmaceutical composition.

The preferred volume of the alcohol is at about 20-60% of the injectable pharmaceutical composition. The preferred alcohol is either a 95% ethanol or dehydrated ethanol.

The preferred volume of polyoxyethylated castor oil is at about 40-60% of the injectable pharmaceutical composition. The preferred polyoxyethylated castor oil is Cremophor® EL or Cremophor® ELP.

The injectable pharmaceutical composition of the present invention is preferably to be used in intravenous injection.

The present invention also provides methods for preparing the injectable pharmaceutical composition. One method comprises the following steps: (1) dissolving paclitaxel in a polyoxyethylated castor oil and alcohol mixture to form a drug mixture; (2) dissolving a sufficient amount of $CO_2$ in an injectable aqueous solution to form a pH$\leq$5.0 injectable aqueous solution; (3) mixing the drug mixture with the pH$\leq$5.0 injectable aqueous solution to form the injectable pharmaceutical composition. The alcohol is preferred to be 95% alcohol or dehydrated alcohol. The polyoxyethylated castor oil is preferred to be Cremophor® EL or Cremophor® ELP. The $CO_2$ is preferred to be in the form of dry ice or $CO_2$ gas or a mixture of both. The amount of $CO_2$ to be dissolved in the injectable pharmaceutical composition at least in an amount of 0.4 mg per mL. The injectable aqueous solution is at no less than about 4% by volume, preferably between about 4 to 10% by volume of the injectable pharmaceutical composition.

The injectable pharmaceutical composition is further filtered to sterilize. The sterilized injectable pharmaceutical composition is then poured into a vial. An adequate amount of $CO_2$ gas, then infused into the residual space of the vial so as to further saturate the injectable pharmaceutical composition and maintaining its acidity before sealing of the vial.

The injectable pharmaceutical composition can also be prepared by (1) dissolving paclitaxel in polyoxyethylated castor oil and alcohol to form a drug mixture; (2) adding an injectable aqueous solution; (3) further dissolving adequate amount of $CO_2$ in the drug mixture to form the injectable pharmaceutical composition. It is preferably that the $CO_2$ is in an amount which can sufficiently to maintain the injectable pharmaceutical composition with a pH about 5.0. The $CO_2$ is preferably in the form of dry ice or $CO_2$ gas or a mixture of both.

The injectable pharmaceutical composition is suitable for treating a patient with cancer, which requires that the injectable pharmaceutical composition to be diluted with an amount of the injectable aqueous solution and then intravenously injecting the diluted injectable pharmaceutical composition to the patient.

The injectable pharmaceutical composition of the present invention is suitable for treating patients with cancer, such as breast cancer, ovarian cancer, lung cancer, melanoma, and lymphoma.

DETAILED DESCRIPTION OF THE INVENTION

Paclitaxel is typically produced as a concentrate or solution in a vehicle suitable for injection in the amount of 6 mg/ml. The vehicle is usually a mixture of ethanol and polyoxyethylated castor oil in the amount of 50:50 by volume.

The currently commercially available paclitaxel include Bristol Myers Squibb's Taxol, Baker Norton's Paclitaxel, Bedford's Paclitaxel, Ivax Pharms's Paclitaxel, Mayne Pharma USA's Paclitaxel, and Mylan's Paclitaxel, all are in formulations containing 6 mg/mL of paclitaxel dissolved in 50:50 (v/v) dehydrated ethanol/polyoxyethylated castor oil. The formulations are recommended to be stored under 2-8° C. During storage, the activity of paclitaxel is known to decrease, which can be detected by HPLC. During long-term storage, paclitaxel in the commercially available products gradually degrades and loses the anti-cancer effect over time.

The present invention provides a novel injectable pharmaceutical composition of paclitaxel, containing, in addition to the active ingredient (i.e., paclitaxel), the co-solvents (i.e., the polyoxyethylated castor oil and alcohol), an injectable aqueous solution, which is infused with $CO_2$. The injectable pharmaceutical composition of the present invention does not contain any organic acids, polyethylene glycol (PEG) or other antioxidants.

The amount of $CO_2$ which is added to the injectable aqueous solution is to bring the pH value of the injectable aqueous solution to 5 or lower, and to make a concentration at least about 0.4 mg of $CO_2$ per mL of the injectable pharmaceutical composition. The adding of $CO_2$ into the injectable pharmaceutical composition has the advantage of acidifying the injectable pharmaceutical composition because $CO_2$ can be dissolved in the injectable aqueous solution and be converted into carbonate ions. An acidic injectable aqueous solution in the injectable pharmaceutical composition has the capability of stabilizing and prolonging the shelf-life of the injectable pharmaceutical composition and protecting the paclitaxel from being degraded.

Figure 1:
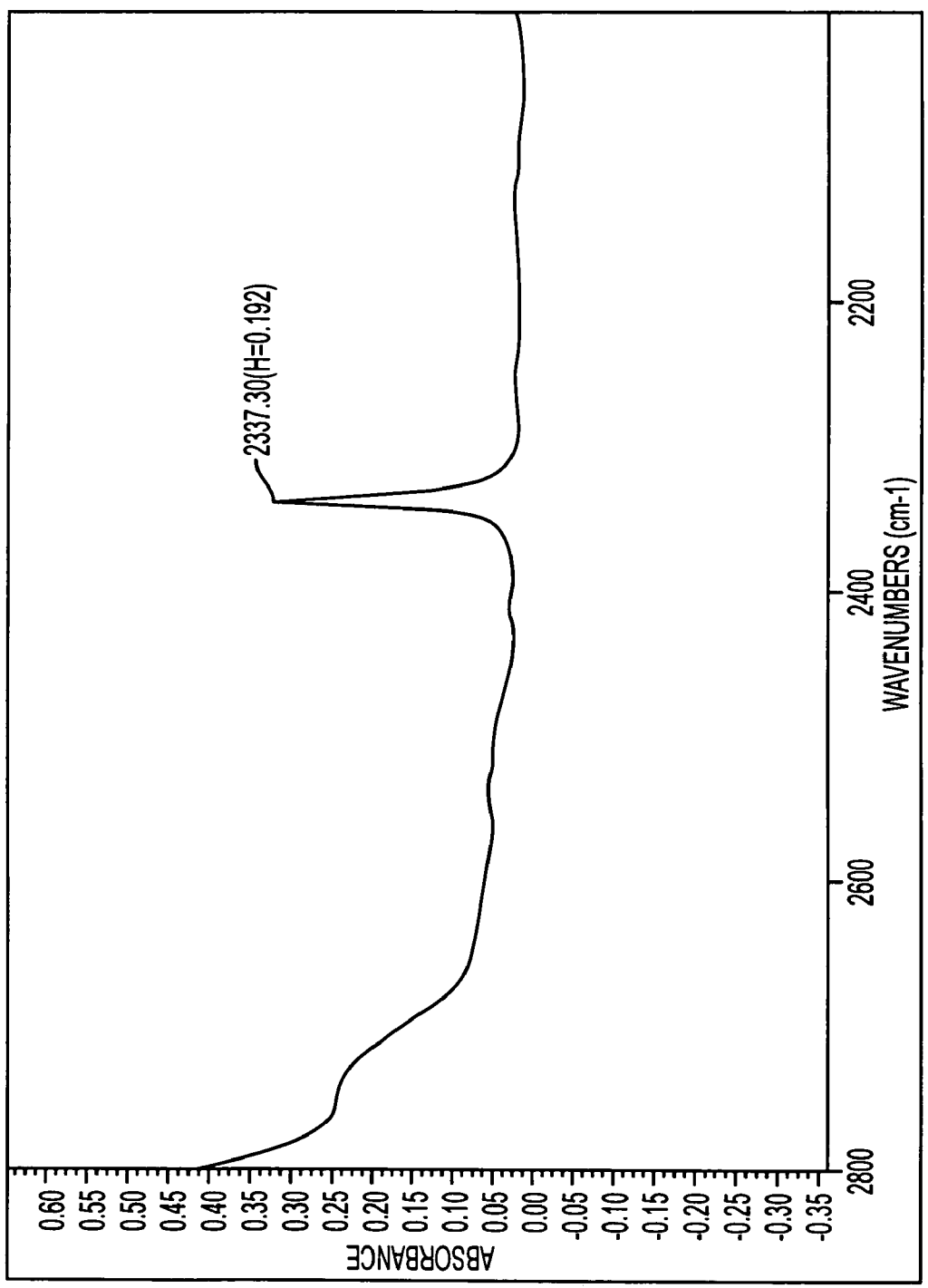
FIG. 1 shows Fourier-Transformed Infrared Spectroscopic (FTIR) spectrum of a Standard solution that is used as a standard reference in the $CO_2$ content determination. The Standard solution, containing a known content of $CO_2$, has an absorption peak at around 2337 wavenumber ($cm^{-1}$). The FTIR spectrum presented in a drawing in which the ordinate is the transmittance in % and the abscissa is the wavelength in $cm^{-1}$.
Figure 2:
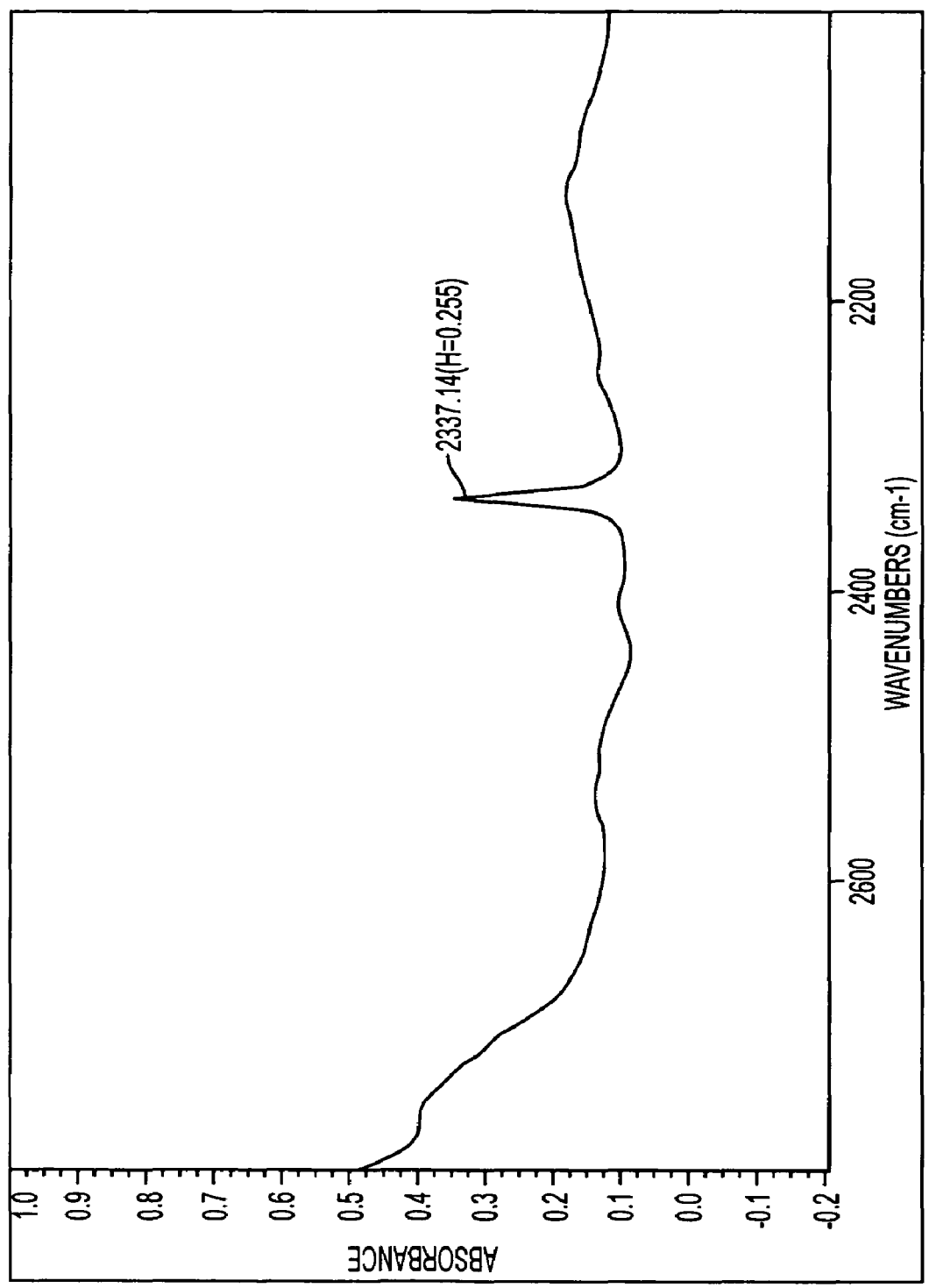
FIG. 2 shows Fourier-Transformed Infrared Spectroscopic (FTIR) spectrum of a Sample solution. The Sample solution contains $CO_2$ and exhibits an absorption peak at around 2337 wavenumber ($cm^{-1}$).

The $CO_2$ content of the injectable pharmaceutical composition is determined using the Fourier-Transformed Infrared Spectroscopic (FTIR) spectrum. A Standard solution of known $CO_2$ content is first prepared. The FTIR absorbances of the Standard solution (FIG. 1) and the Sample solution (FIG. 2) at a wavenumber of about 2337 $cm^{-1}$ are then measured against another Paclitaxel Injection (containing no $CO_2$) as a blank reference. As shown in FIGS. 1 and 2, both spectra showed an absorption peak at about 2237 wavenumber ($cm^{-1}$). The $CO_2$ content of the Sample solution is calculated by comparing the absorbances of the Standard solution and the Sample solution and deriving from the known $CO_2$ content of the Standard solution.

The injectable pharmaceutical composition of the present invention remains stable at a temperature as high as 40° C. for at least 1 month, and the content and quality of paclitaxel in the injectable pharmaceutical composition remains unchanged (as shown in Table 1). In addition, when the injectable pharmaceutical composition is diluted with 0.9% (w/v) NaCl solution (i.e., normal saline solution), 5% dextrose (D5W, w/v) in water, or 5% dextrose (w/v) in 0.9% NaCl (w/v) solution, the diluted injectable pharmaceutical solution is stable at room temperature for about 28 hours (as shown in Table 2). These results demonstrate that the paclitaxel in the injectable pharmaceutical composition of the present invention is better preserved and less likely to be decomposed than the commercial products of paclitaxel injectable solution.

The injectable pharmaceutical composition of the present invention comprises about 0.01-1% by weight of paclitaxel, about 40-60% by volume of polyoxyethylated castor oil, about 20-60% by volume of alcohol, and at least about 4% by volume of water.

The preferred polyoxyethylated castor oil includes Cremophor® EL and Cremophor® ELP. Cremophor is the tradename of BASF's (Badische Anilin und Soda Fabrik AG, Ludwigshafen, Federal Republic of Germany) polyoxyethylated castor oil. Its Cremophor® grades include Cremophor® A 25, Cremophor® EL, Cremophor® RH40, Cremophor® A6, and Cremophor® ELP. Cremophor® EL is a nonionic solubilizer and emulsifier manufactured by reacting castor oil with ethylene oxide in a molar ratio of 1 to 35. Cremophor® ELP is manufactured by purifying Cremophor® EL and is therefore suitable for parenteral applications, e.g., paclitaxel preparation. The preferred alcohol includes dehydrated alcohol (dehydrated ethanol) and 95% alcohol (ethanol). The preferred injectable aqueous solution is water, which is preferably to be filtered and sterilized.

The following examples are illustrative, but not limiting the scope of the present invention. Reasonable variations, such as those occur to reasonable artisan, can be made herein without departing from the scope of the present invention.

EXAMPLE 1

(A) Composition:

| Ingredient | Amount per vial |
| --- | --- |
| 1. Paclitaxel | 30 mg |
| 2. Cremophor ® ELP (polyoxyethylated castor oil) | 2,635 mg |
| 3. Dehydrated Alcohol | q.s. |
| 4. $CO_2$ (dry ice in Example 1-1; gas in Example 1-2) | q.s. to adjust the pH value of the injectable aqueous solution to no higher than about 5.0 |
| 5. Water for Injection | 0.2 mL |
| Total Volume | 5 mL |

(B) Preparation:
(1) The carbon dioxide ($CO_2$) solid (dry ice, Example 1-1) or gas (Example 1-2) was added to the Water for Injection (i.e., the preferred injectable aqueous solution) and thoroughly mixed. The pH of the mixture was measured to ensure that the pH value of the Water for Injection was $\leq 5.0$.
(2) Paclitaxel, Cremophor® ELP and a small volume of the dehydrated alcohol were thoroughly mixed until paclitaxel was completely dissolved.
(3) Item (1) was added to Item (2) and mixed uniformly, then q.s. to the full volume using the rest of the allocated volume of the dehydrated alcohol as indicated in (A).
(4) Item (3) was poured into a vial and sealed.

EXAMPLE 2

(A) Composition:

| Ingredient | Amount per vial |
| --- | --- |
| 1. Paclitaxel | 30 mg |
| 2. Cremophor ® ELP (polyoxyethylated castor oil) | 2,635 mg |
| 3. Dehydrated Alcohol | q.s. |
| 4. $CO_2$ (dry ice in Example 2-1; gas in Example 2-2) | q.s. to adjust the pH value of the injectable aqueous solution to no higher than about 5.0 |
| 5. Water for Injection | 0.3 mL |
| Total Volume | 5 mL |

(B) Preparation:
(1) The carbon dioxide ($CO_2$) solid (dry ice, Example 2-1) or gas (Example 2-2) was added to the Water for Injection and thoroughly mixed. The pH value of the mixture was measured to ensure that the pH of the Water for Injection (i.e., the preferred injectable aqueous solution) was $\leq 5.0$.
(2) Paclitaxel, Cremophor® ELP and a small volume of the dehydrated alcohol were thoroughly mixed until paclitaxel was completely dissolved.
(3) Item (1) was added to Item (2) and mixed uniformly, then q.s. to the full volume using the rest of the allocated volume of the dehydrated alcohol as indicated in (A).
(4) Item (3) was poured into a vial and sealed.

EXAMPLE 3

(A) Composition:

| Ingredient | Amount per vial |
| --- | --- |
| 1. Paclitaxel | 30 mg |
| 2. Cremophor ® ELP (polyoxyethylated castor oil) | 2,635 mg |
| 3. Dehydrated Alcohol | q.s. |
| 4. $CO_2$ (gas in Example 3-1; dry ice and gas in Example 3-2) | q.s. to adjust the pH value of the injectable aqueous solution to no higher than about 5.0 |
| 5. Water for Injection | 0.2 mL |
| Total Volume | 5 mL |

(B) Preparation:
1. The carbon dioxide ($CO_2$) gas (Example 3-1) or both dry ice and gas (Example 3-2) was added to the Water for Injection (i.e., the preferred injectable aqueous solution) and thoroughly mixed. The pH value of the mixture was measured to ensure that the pH of the Water for Injection was $\leq 5.0$.
2. Paclitaxel, Cremophor® ELP and a small volume of the dehydrated alcohol were thoroughly mixed until paclitaxel was completely dissolved.
3. Item (1) was added to Item (2) and mixed uniformly, then q.s. to the full volume using the rest of the allocated volume of the dehydrated alcohol as indicated in (A).
4. Item (3) was poured into a vial, and $CO_2$ gas was infused into the vial before the vial was sealed.

EXAMPLE 4

(A) Composition:

| Ingredient | Amount per vial |
| --- | --- |
| 1. Paclitaxel | 30 mg |
| 2. Cremophor ® ELP (polyoxyethylated castor oil) | 2,635 mg |
| 3. Dehydrated Alcohol | q.s. |
| 4. $CO_2$ (gas and dry ice in Example 4-1; gas in Example 4-2) | q.s. to adjust the pH value of the injectable aqueous solution to no higher than about 5.0 |
| 5. Water for Injection | 0.3 mL |
| Total Volume | 5 mL |

(B) Preparation:
1. The carbon dioxide ($CO_2$) gas and solid (Example 4-1) or gas (Example 4-2) was added to the Water for Injection (i.e., the preferred injectable aqueous solution) and thoroughly mixed. The pH value of the mixture was measured to ensure that the pH of the Water for Injection was $\leq 5.0$.
2. Paclitaxel, Cremophor® ELP and a small volume of the dehydrated alcohol were thoroughly mixed until paclitaxel was completely dissolved.
3. Item (1) was added to Item (2) and mixed uniformly, then q.s. to the full volume using the rest of the allocated volume of the dehydrated alcohol as indicated in (A).
4. Item (3) was poured into a vial, and $CO_2$ gas was infused into the vial before the vial was sealed.

EXAMPLE 5

(A) Composition:

| Ingredient | Amount per vial |
| --- | --- |
| 1. Paclitaxel | 30 mg |
| 2. Cremophor ® ELP (polyoxyethylated castor oil) | 2,635 mg |
| 3. Dehydrated Alcohol | q.s. |
| 4. $CO_2$ (solid and gas) | q.s. to adjust the pH value of the injectable aqueous solution to no higher than about 5.0 |
| 5. Water for Injection | 0.2 mL |
| Total Volume | 5 mL |

(B) Preparation:
1. Paclitaxel, Cremophor® ELP and a small volume of dehydrated alcohol were thoroughly mixed until paclitaxel was completely dissolved, then Water for Injection (i.e., the preferred injectable aqueous solution) was added to the above solution and mixed well.
2. The $CO_2$ (gas and dry ice) was added to Item (1) and uniformly mixed.
3. The rest of the allocated dehydrated alcohol was added to Item (2) to bring the volume to the full volume.
4. Item (3) was poured into a vial and sealed.

EXAMPLE 6

(A) Composition:

| Ingredient | Amount per vial |
| --- | --- |
| 1. Paclitaxel | 30 mg |
| 2. Cremophor ® ELP (polyoxyethylated castor oil) | 2,635 mg |
| 3. Dehydrated Alcohol | q.s. |
| 4. $CO_2$ (solid and gas) | q.s. to adjust the pH value of the injectable aqueous solution to no higher than about 5.0 |
| 5. Water for Injection | 0.3 mL |
| Total Volume | 5 mL |

(B) Preparation:
1. Paclitaxel, Cremophor® ELP and a small volume of dehydrated alcohol were thoroughly mixed until paclitaxel was completely dissolved, then Water for Injection (i.e., the preferred injectable aqueous solution) was added to the above solution and mixed well.
2. The $CO_2$ (gas and dry ice) was added to Item (1) and uniformly mixed.
3. The rest of the allocated dehydrated alcohol was added to Item (2) to bring the volume to the full volume.
4. Item (3) was poured into a vial and sealed.

EXAMPLE 7

(A) Composition:

| Ingredient | Amount per vial |
|---|---|
| 1. Paclitaxel | 30 mg |
| 2. Cremophor ® ELP (polyoxyethylated castor oil) | 2,635 mg |
| 3. Alcohol (95%) | q.s. |
| 4. $CO_2$ (dry ice in Example 7-1; gas in Example 7-2) | q.s. to adjust the pH value of the injectable aqueous solution to no higher than about 5.0 |
| 5. Water for Injection | 0.1 mL |
| Total Volume | 5 mL |

(B) Preparation:
(1) The carbon dioxide ($CO_2$) solid/dry ice (Example 7-1) or gas (Example 7-2) was added to the Water for Injection (i.e., the preferred injectable aqueous solution) and thoroughly mixed. The pH value of the mixture was measured to ensure that the pH of the Water for Injection was ≦5.0.
(2) Paclitaxel, Cremophor® ELP and a small volume of the alcohol (95%) were thoroughly mixed until paclitaxel was completely dissolved.
(3) Item (1) was added to Item (2) and mixed uniformly, then q.s. to the full volume using the rest of the allocated volume of the alcohol (95%) as indicated in (A).
(4) Item (3) was poured into a vial and sealed.

EXAMPLE 8

(A) Composition:

| Ingredient | Amount per vial |
|---|---|
| 1. Paclitaxel | 30 mg |
| 2. Cremophor ® EL (polyoxyethylated castor oil) | 2,635 mg |
| 3. Alcohol (95%) | q.s. |
| 4. $CO_2$ (dry ice and gas) | q.s. to adjust the pH value of the injectable aqueous solution to no higher than about 5.0 |
| 5. Water for Injection | 0.1 mL |
| Total Volume | 5 mL |

(B) Preparation:
(1) Paclitaxel, Cremophor® EL and a small volume of alcohol (95%) were thoroughly mixed until paclitaxel was completely dissolved, then Water for Injection (i.e., the preferred injectable aqueous solution) was added to the above solution and mixed well.
(2) The $CO_2$ (gas and dry ice) was added to Item (1) and uniformly mixed.
(3) The rest of the allocated alcohol (95%) was added to Item (2) to bring the volume to the full volume.
(4) Item (3) was poured into a vial, and $CO_2$ gas was infused into the vial before the vial was sealed.

EXAMPLE 9

(A) Composition:

| Ingredient | Amount per vial |
|---|---|
| 1. Paclitaxel | 30 mg |
| 2. Cremophor ® EL (polyoxyethylated castor oil) | 2,635 mg |
| 3. Alcohol (95%) | q.s. |
| 4. $CO_2$ (dry ice) | q.s. to adjust the pH value of the injectable aqueous solution to no higher than about 5.0 |
| 5. Water for Injection | 0.1 mL |
| Total Volume | 5 mL |

(B) Preparation:
(1) Paclitaxel, Cremophor® EL and a small volume of Alcohol (95%) were thoroughly mixed until paclitaxel was completely dissolved, then Water for Injection (i.e., the preferred injectable aqueous solution) was added to the above solution and mixed well.
(2) The $CO_2$ (dry ice) was added to Item (1) and uniformly mixed.
(3) The rest of the allocated Alcohol (95%) was added to Item (2) to bring the volume to the full volume.
(4) Item (3) was poured into a vial and sealed.

Stability Test 1

EXAMPLES 1-9 (for a total of 14 examples) were placed at 40° C. for 1-month. The samples were then assayed to determine the following: (1) total content; (2) pH of the composition (determined after diluting the composition 10 times with water); (3) appearance of the composition; (4) sterility; (5) pyrogen; (6) impurity; and (7) total water content. The results are shown in Table 1.

The results demonstrate: (1) that no weight loss or appearance change was detected during the expedited shelf life test; (2) that the pH of all of the examples maintained at about 5.0; (3) that no bacterial contamination was detected; (4) that no pyrogen was detected; (5) that the impurity in all of the examples tested was within 1.2%; and (5) that the total water content in each of the Examples was between 4 to 10% by volume of the entire injectable pharmaceutical composition. The results confirm that the injectable pharmaceutical composition of the present invention remained stable after storage under 40° C. for 1-month.

TABLE 1

Examples 1-9 and Test Results after Storage under 40° for 1-month

| | | | Examples | | | | | | |
|---|---|---|---|---|---|---|---|---|---|
| | | | 1-1 | 1-2 | 2-1 | 2-2 | 3-1 | 3-2 | 4-1 |
| Composition | Paclitaxel | | 30 mg | 30 mg | 30 mg | 30 mg | 30 mg | 30 mg | 30 mg |
| | CREMOPHOR ® ELP | | 2,635 mg | 2,635 mg | 2,635 mg | 2,635 mg | 2,635 mg | 2,635 mg | 2,635 mg |
| | CREMOPHOR ® EL | | | | | | | | |

TABLE 1-continued

Examples 1-9 and Test Results after Storage under 40° for 1-month

|  |  |  |  |  |  |  |  |  |
|---|---|---|---|---|---|---|---|---|
|  | Alcohol (95%) | — | — | — | — | — | — | — |
|  | Dehydrated Alcohol | q.s. | q.s. | q.s. | q.s. | q.s. | q.s. | q.s. |
|  | Water For Injection | 0.2 mL | 0.2 mL | 0.3 mL | 0.3 mL | 0.2 mL | 0.2 mL | 0.3 mL |
|  | $CO_2$ solid | adq. amt. |  | adq. amt. |  |  | adq. amt. | adq. amt. |
|  | gas |  | adq. amt. |  | adq. amt. | adq. amt. | adq. amt. | adq. amt. |
|  | Total amount | 5 mL | 5 mL | 5 mL | 5 mL | 5 mL | 5 mL | 5 mL |
| Results | Assay (% of original) | 101.3 | 101.8 | 102.5 | 103.1 | 102.0 | 103.5 | 103.5 |
|  | pH after 10 fold dilution of the product | 5.0 | 5.14 | 5.32 | 4.82 | 5.3 | 5.0 | 4.93 |
|  | Appearance | clear thick liquid | same as left | same as left | same as left | same as left | same as left | same as left |
|  | Sterility test | negative | same as left | same as left | same as left | same as left | same as left | same as left |
|  | Pyrogen test | negative | same as left | same as left | same as left | same as left | same as left | same as left |
|  | Total impurity | 1.21% | 1.09% | 1.12% | 1.28% | 1.16% | 1.18% | 1.25% |
|  | Water content | 4.582% | 4.554% | 6.515% | 6.551% | 4.324% | 4.668% | 6.588% |

|  |  | Examples |  |  |  |  |  |  |
|---|---|---|---|---|---|---|---|---|
|  |  | 4-2 | 5 | 6 | 7-1 | 7-2 | 8 | 9 |
| Composition | Paclitaxel | 30 mg | 30 mg | 30 mg | 30 mg | 30 mg | 30 mg | 30 mg |
|  | CREMOPHOR ® ELP | 2,635 mg | 2,635 mg | 2,635 mg | 2,635 mg | 2,635 mg |  |  |
|  | CREMOPHOR ® EL |  |  |  |  |  | 2,635 mg | 2,635 mg |
|  | Alcohol (95%) | — | — | — | q.s. | q.s. | q.s. | q.s. |
|  | Dehydrated Alcohol | q.s. | q.s. | q.s. | — | — | — | — |
|  | Water For Injection | 0.3 mL | 0.2 mL | 0.3 mL | 0.1 mL | 0.1 mL | 0.1 mL | 0.1 mL |
|  | $CO_2$ solid |  | adq. amt. | adq. amt. | adq. amt. |  | adq. amt. | adq. amt. |
|  | gas | adq. amt. | adq. amt. | adq. amt. |  | adq. amt. | adq. amt. | adq. amt. |
|  | Total amount | 5 mL | 5 mL | 5 mL | 5 mL | 5 mL | 5 mL | 5 mL |
| Results | Assay (% of original) | 101.8 | 99.7 | 99.9 | 101.1 | 100.4 | 101.5 | 99.6 |
|  | pH after 10 fold dilution of the product | 5.14 | 5.3 | 5.21 | 4.94 | 4.92 | 5.07 | 5.21 |
|  | Appearance | same as left | same as left | same as left | same as left | same as left | same as left | same as left |
|  | Sterility test | same as left | same as left | same as left | same as left | same as left | same as left | same as left |
|  | Pyrogen test | same as left | same as left | same as left | same as left | same as left | same as left | same as left |
|  | Total impurity | 1.09% | 1.09% | 1.21% | 0.9% | 1.04% | 1.02% | 1.20% |
|  | Water content | 6.554% | 4.93% | 6.28% | 5.7% | 6.0% | 5.8% | 5.9% | adq. amt.: adequate amount

Stability Test 2

Stability of the pharmaceutical composition of the present invention after dilution was studied. Samples of Example 2-1 were diluted with 0.9% NaCl or 5% Dextrose in water or in 0.9% NaCl/5% Dextrose mixture solution to a final concentration of 0.3 mg/mL of paclitaxel. The samples were stored at room temperature for 28 hours and the content of paclitaxel was determined at 0, 20, and 28 hours. The results (expressed as % of original paclitaxel content) indicated that the pharmaceutical composition of the present invention remained stable after dilution for at least 28 hours when stored at room temperature (Table 2).

TABLE 2

Stability of the Injectable Paclitaxel Pharmaceutical Composition after Dilution with 0.9% NaCl, 5% Dextrose, or 0.9% NaCl/5% Dextrose and Storage at Room Temperature for 28 Hours

| Time after dilution | 0.9% NaCl | 5% Dextrose | 0.9% NaCl/5% Dextrose mixture solution |
|---|---|---|---|
| 0 hr | 100.0 | 100.0 | 100.0 |
| 20 hrs | 97.8 | 98.6 | 97.5 |
| 28 hrs | 96.0 | 96.6 | 96.9 |

While the invention has been described by way of examples and in term of the preferred embodiments, it is to be understood that the invention is not limited to the disclosed embodiments. On the contrary, it is intended to cover various modifications as would be apparent to those skilled in the art. Therefore, the scope of the appended claims should be accorded the broadest interpretation so as to encompass all such modifications.

We claim:

1. An injectable pharmaceutical composition comprising:
   0.01-1% by weight paclitaxel;
   40-60% by volume of a polyoxyethylated castor oil;
   20-60% by volume of an alcohol; and
   no less than 4% by volume of an injectable aqueous solution;
   wherein a sufficient amount of $CO_2$ is added to said injectable pharmaceutical composition; wherein said sufficient amount of said $CO_2$ is at a concentration of 0.4 mg of said $CO_2$ per mL of said injectable pharmaceutical composition.

2. The injectable pharmaceutical composition according to claim 1, wherein said $CO_2$ is in the form of dry ice or $CO_2$ gas or a mixture thereof.

3. The injectable pharmaceutical composition according to claim 1, wherein said injectable aqueous solution is water.

4. The injectable pharmaceutical composition according to claim 1, wherein said alcohol is 95% ethanol or dehydrated ethanol.

5. The injectable pharmaceutical composition according to claim 1, wherein said pharmaceutical composition is administered through intravenous injection.

6. A method for preparing an injectable pharmaceutical composition according to claim 1 comprising:
   dissolving paclitaxel in polyoxyethylated castor oil and alcohol to form a drug mixture;
   dissolving said $CO_2$ in said injectable aqueous solution to form a pH $\leq 5.0$ injectable aqueous solution;
   mixing said drug mixture with said pH $\leq 5.0$ injectable aqueous solution to form said injectable pharmaceutical composition.

7. The method according to claim 6, wherein said alcohol is 95% alcohol or dehydrated alcohol.

8. The method according to claim 6, wherein said $CO_2$ is in the form of dry ice or $CO_2$ gas or a mixture thereof.

9. The method according to claim 6, further comprising:
   filtering said injectable pharmaceutical composition to form a sterile injectable pharmaceutical composition;
   either pouring said sterile injectable pharmaceutical composition into a vial and seal or further infusing $CO_2$ gas into said vial.

10. A method for preparing an injectable pharmaceutical composition according to claim 1 comprising:
    dissolving said paclitaxel in polyoxyethylated castor oil and alcohol to form a drug mixture;
    adding said injectable aqueous solution to said drug mixture;
    adding said $CO_2$ to the drug mixture to make said injectable pharmaceutical composition with a pH about 5.0.

11. The method according to claim 10, wherein said $CO_2$ is in a form of dry ice or gas or a mixture thereof.

12. The method according to claim 10, comprising:
    filtering said injectable pharmaceutical composition to form a sterile injectable pharmaceutical composition;
    either pouring said sterile injectable pharmaceutical composition into a vial and seal or further infusing $CO_2$ gas into said vial.

13. A method for treating a patient with cancer comprising:
    diluting said injectable pharmaceutical composition according to claim 1 with a dilution solution to form a diluted injectable pharmaceutical composition; and intravenously injecting said diluted injectable pharmaceutical composition to said patient.

14. The method according to claim 13, wherein said dilution solution is a 0.9% NaCl solution (w/v), a 5% dextrose in water (w/v), or a 5% dextrose in a 0.9% NaCl solution (w/v).

15. The method according to claim 13, wherein said cancer is breast cancer, ovarian cancer, lung cancer, melanoma, and lymphoma.

* * * * *